United States Patent
Saito

(10) Patent No.: US 11,375,928 B2
(45) Date of Patent: Jul. 5, 2022

(54) ENDOSCOPE SYSTEM

(71) Applicant: FUJIFILM Corporation, Tokyo (JP)

(72) Inventor: Takaaki Saito, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/986,885

(22) Filed: Aug. 6, 2020

(65) Prior Publication Data

US 2020/0359940 A1 Nov. 19, 2020

Related U.S. Application Data

(63) Continuation of application No. PCT/JP2019/000502, filed on Jan. 10, 2019.

(30) Foreign Application Priority Data

Feb. 9, 2018 (JP) .............................. JP2018-022517

(51) Int. Cl.
*A61B 5/1459* (2006.01)
*A61B 1/04* (2006.01)
(Continued)

(52) U.S. Cl.
CPC .............. *A61B 5/1459* (2013.01); *A61B 1/04* (2013.01); *A61B 5/14552* (2013.01);
(Continued)

(58) Field of Classification Search
CPC ............ A61B 1/00006; A61B 1/00009; A61B 1/00045; A61B 1/00117; A61B 1/00186;
(Continued)

(56) References Cited

U.S. PATENT DOCUMENTS 9,801,573 B2 * 10/2017 Saito ..................... A61B 1/0638
2007/0219439 A1 * 9/2007 Vilser ................ A61B 5/14546
600/323
(Continued)

FOREIGN PATENT DOCUMENTS

JP 2012143399 A 8/2012
JP 2013099464 A 5/2013
(Continued)

OTHER PUBLICATIONS

International Search Report issued in PCT/JP2019/000502; dated Mar. 26, 2019.
(Continued)

*Primary Examiner* — Peter D Le
(74) *Attorney, Agent, or Firm* — Studebaker & Brackett PC

(57) ABSTRACT

An endoscope system includes: an image acquiring unit that acquires a first frame image obtained by photographing a photographic subject and a second frame image obtained by photographing the photographic subject at a timing different from that of the first frame image; an oxygen saturation calculating unit that calculates an oxygen saturation by using the first frame image and the second frame image; a reliability calculating unit that calculates reliability of the oxygen saturation, calculated by the oxygen calculating unit, by using a signal ratio that is a ratio between a pixel value in a first specific wavelength range corresponding to a specific wavelength range of the first frame image and a pixel value in a second specific wavelength range corresponding to the specific wavelength range of the second frame image; and an information amount adjusting unit that adjusts an information amount of the oxygen saturation by using the reliability.

8 Claims, 9 Drawing Sheets

(51) Int. Cl.
    *A61B 5/1455*     (2006.01)
    *A61B 5/00*     (2006.01)
    *G06T 7/00*     (2017.01)
    *H04N 5/225*     (2006.01)
    *A61B 1/00*     (2006.01)
    *A61B 1/06*     (2006.01)
    *A61B 1/07*     (2006.01)

(52) U.S. Cl.
    CPC .......... *A61B 5/7221* (2013.01); *A61B 5/7278* (2013.01); *G06T 7/0016* (2013.01); *H04N 5/2256* (2013.01); *A61B 1/00006* (2013.01); *A61B 1/00045* (2013.01); *A61B 1/00117* (2013.01); *A61B 1/063* (2013.01); *A61B 1/0669* (2013.01); *A61B 1/0684* (2013.01); *A61B 1/07* (2013.01); *G06T 2207/10068* (2013.01); *G06T 2207/10152* (2013.01); *H04N 2005/2255* (2013.01)

(58) Field of Classification Search
    CPC ....... A61B 1/00188; A61B 1/04; A61B 1/045; A61B 1/05; A61B 1/063; A61B 1/0653; A61B 1/0669; A61B 1/0684; A61B 1/07; A61B 5/14552; A61B 5/1459; A61B 5/7221; A61B 5/7278; G06T 2207/10024; G06T 2207/10068; G06T 2207/10152; G06T 2207/30104; G06T 7/0016; H04N 2005/2255; H04N 5/2256; H04N 7/18
    See application file for complete search history.

(56) References Cited

U.S. PATENT DOCUMENTS

| | | | | |
|---|---|---|---|---|
| 2011/0077462 | A1* | 3/2011 | Saitou | A61B 1/063 600/109 |
| 2011/0237882 | A1* | 9/2011 | Saito | A61B 5/0084 600/109 |
| 2011/0237883 | A1* | 9/2011 | Chun | A61B 1/0638 600/109 |
| 2012/0157768 | A1* | 6/2012 | Saito | A61B 5/14551 600/109 |
| 2012/0179013 | A1* | 7/2012 | Saito | A61B 1/00009 600/339 |
| 2013/0030268 | A1* | 1/2013 | Saito | A61B 1/0653 600/325 |
| 2013/0113906 | A1 | 5/2013 | Saito | |
| 2013/0235177 | A1 | 9/2013 | Saito | |
| 2013/0245411 | A1* | 9/2013 | Saito | A61B 1/045 600/339 |
| 2015/0201871 | A1* | 7/2015 | Shiraishi | A61B 5/1459 600/339 |
| 2015/0216460 | A1 | 8/2015 | Shigeta | |
| 2015/0238086 | A1* | 8/2015 | Saito | A61B 1/0638 600/339 |
| 2017/0098301 | A1* | 4/2017 | Ikemoto | G06T 7/0012 |
| 2018/0000335 | A1* | 1/2018 | Igarashi | H04N 5/2354 |
| 2018/0235527 | A1* | 8/2018 | Yamamoto | A61B 1/00188 |
| 2018/0368658 | A1 | 12/2018 | Yamamoto | |
| 2019/0008374 | A1* | 1/2019 | Yamamoto | A61B 1/051 |
| 2019/0117055 | A1* | 4/2019 | Ito | A61B 1/05 |
| 2019/0223703 | A1* | 7/2019 | Fukuda | G02B 23/2461 |
| 2019/0223705 | A1* | 7/2019 | Fukuda | G02B 23/26 |
| 2019/0239735 | A1* | 8/2019 | Fukuda | A61B 1/00009 |
| 2019/0282135 | A1* | 9/2019 | Ito | A61B 1/00006 |

FOREIGN PATENT DOCUMENTS

| | | |
|---|---|---|
| JP | 2013188244 A | 9/2013 |
| JP | 2015146924 A | 8/2015 |
| WO | 2016136698 A1 | 9/2016 |
| WO | 2017154292 A1 | 9/2017 |

OTHER PUBLICATIONS

International Preliminary Report on Patentability and Written Opinion issued in PCT/JP2019/000502; dated Aug. 11, 2020.

* cited by examiner

| ILLUMINATION LIGHT | FIRST WHITE LIGHT W1 | SECOND WHITE LIGHT W2 |
|---|---|---|
| ACQUIRED IMAGE | FIRST FRAME IMAGE (B1 IMAGE / G1 IMAGE / R1 IMAGE) | SECOND FRAME IMAGE (B2 IMAGE / G2 IMAGE / R2 IMAGE) |

ENDOSCOPE SYSTEM

CROSS-REFERENCE TO RELATED APPLICATIONS

This application is a Continuation of PCT International Application No. PCT/JP2019/000502 filed on 10 Jan. 2019, which claims priority under 35 U.S.C. § 119(a) to Japanese Patent Application No. 2018-022517 filed on 9 Feb. 2018. The above application is hereby expressly incorporated by reference, in its entirety, into the present application.

BACKGROUND OF THE INVENTION

1. Field of the Invention

The present invention relates to an endoscope system that calculates an oxygen saturation.

2. Description of the Related Art

In the medical field, an endoscope system including a light source device, an endoscope, and a processor device is widely used. In particular, in recent years, the following endoscope system has been known. The endoscope system not only photographs an external appearance of a photographic subject that is an observation target for observation but also calculates biological information such as an oxygen saturation by using a captured image of the photographic subject. The oxygen saturation is calculated by arithmetic processing or the like using an image captured by using illumination light whose absorption coefficient changes in accordance with the oxygen saturation of hemoglobin.

In addition, an endoscope system has been known in which reliability representing the accuracy of a calculated oxygen saturation, and if an oxygen saturation image representing the oxygen saturation is generated, display color for a part with low reliability is made close to monochrome, thereby changing an information amount of the displayed oxygen saturation (JP2012-143399A (corresponding to US 2012/0179013A1)). Specifically, in the endoscope system according to JP2012-143399A, first reliability is obtained by using a pixel value of an image used for calculating the oxygen saturation. In addition, second reliability is obtained in accordance with the position of the pixel. The first reliability indicates that the calculation accuracy of the oxygen saturation is low for, for example, a part where halation occurs or a signal-to-noise ratio (S/N ratio) is small because of extremely low brightness. The second reliability indicates that the calculation accuracy of the oxygen saturation is low because of light amount distribution of illumination light. In the endoscope system according to JP2012-143399A, by using the first reliability, the second reliability, or both the first reliability and the second reliability, the display color of the oxygen saturation in the oxygen saturation image is changed.

SUMMARY OF THE INVENTION

As disclosed in JP2012-143399A, the calculation accuracy of the oxygen saturation decreases due to a halation part, a dark part, light amount distribution of illumination light, or a complex factor of these. There are other factors that decrease the calculation accuracy of the oxygen saturation. Specifically, if a photographic subject moves or a relative movement occurs between the photographic subject and an endoscope, the accuracy of the oxygen saturation decreases. This is because images captured in two frames are typically used for calculating the oxygen saturation.

An object of the present invention is to provide an endoscope system that adjusts an information amount of the oxygen saturation in accordance with the accuracy thereof even if the photographic subject moves or a relative movement occurs between the photographic subject and the endoscope.

An endoscope system according to the present invention includes: an image acquiring unit that acquires a first frame image obtained by photographing a photographic subject and a second frame image obtained by photographing the photographic subject at a timing different from that of the first frame image; an oxygen saturation calculating unit that calculates an oxygen saturation by using the first frame image and the second frame image; a reliability calculating unit that calculates reliability of the oxygen saturation, calculated by the oxygen calculating unit, by using a signal ratio that is a ratio between a pixel value in a first specific wavelength range corresponding to a specific wavelength range of the first frame image and a pixel value in a second specific wavelength range corresponding to the specific wavelength range of the second frame image; and an information amount adjusting unit that adjusts an information amount of the oxygen saturation by using the reliability.

It is preferable that the reliability calculating unit calculate the reliability by using the signal ratio, a pixel value of the first frame image, and a pixel value of the second frame image.

It is preferable that the reliability calculating unit calculate first reliability by using the signal ratio, calculates second reliability by using the pixel value of the first frame image and the pixel value of the second frame image, and output, as the reliability, a minimum out of the first reliability and the second reliability.

It is preferable that the first reliability be a constant value if a value of the signal ratio falls within a first specific range including a specific value and gradually decrease as the value of the signal ratio is more away from the specific value if the value of the signal ratio falls out of the first specific range.

It is preferable that the second reliability be a constant value if the pixel value of the first frame image and the pixel value of the second frame image fall within a second specific range and be zero if one or more of the pixel value of the first frame image and the pixel value of the second frame image fall out of the second specific range.

It is preferable that the specific wavelength range be a green wavelength range or a red wavelength range.

It is preferable that the reliability calculating unit calculate the reliability by further using a ratio between a pixel value of the first frame image and a pixel value of the second frame image corresponding to different wavelength ranges.

It is preferable that the reliability calculating unit calculate the reliability by using a second signal ratio that is a ratio between a pixel value of the first frame image or a pixel value of the second frame image corresponding to a red wavelength range and a pixel value of the first frame image or a pixel value of the second frame image corresponding to a green wavelength range.

It is preferable that the reliability calculating unit calculate the reliability by using a third signal ratio that is a ratio between a pixel value of the first frame image or a pixel value of the second frame image corresponding to a blue wavelength range and a pixel value of the first frame image or a pixel value of the second frame image corresponding to a green wavelength range.

It is preferable that the first frame image and the second frame image be successively captured.

According to the endoscope system according to the present invention, it is possible to adjust the information amount of the oxygen saturation in accordance with the accuracy thereof even if the photographic subject moves or a relative movement occurs between the photographic subject and the endoscope.

DESCRIPTION OF THE PREFERRED EMBODIMENTS

First Embodiment

Figure 1:
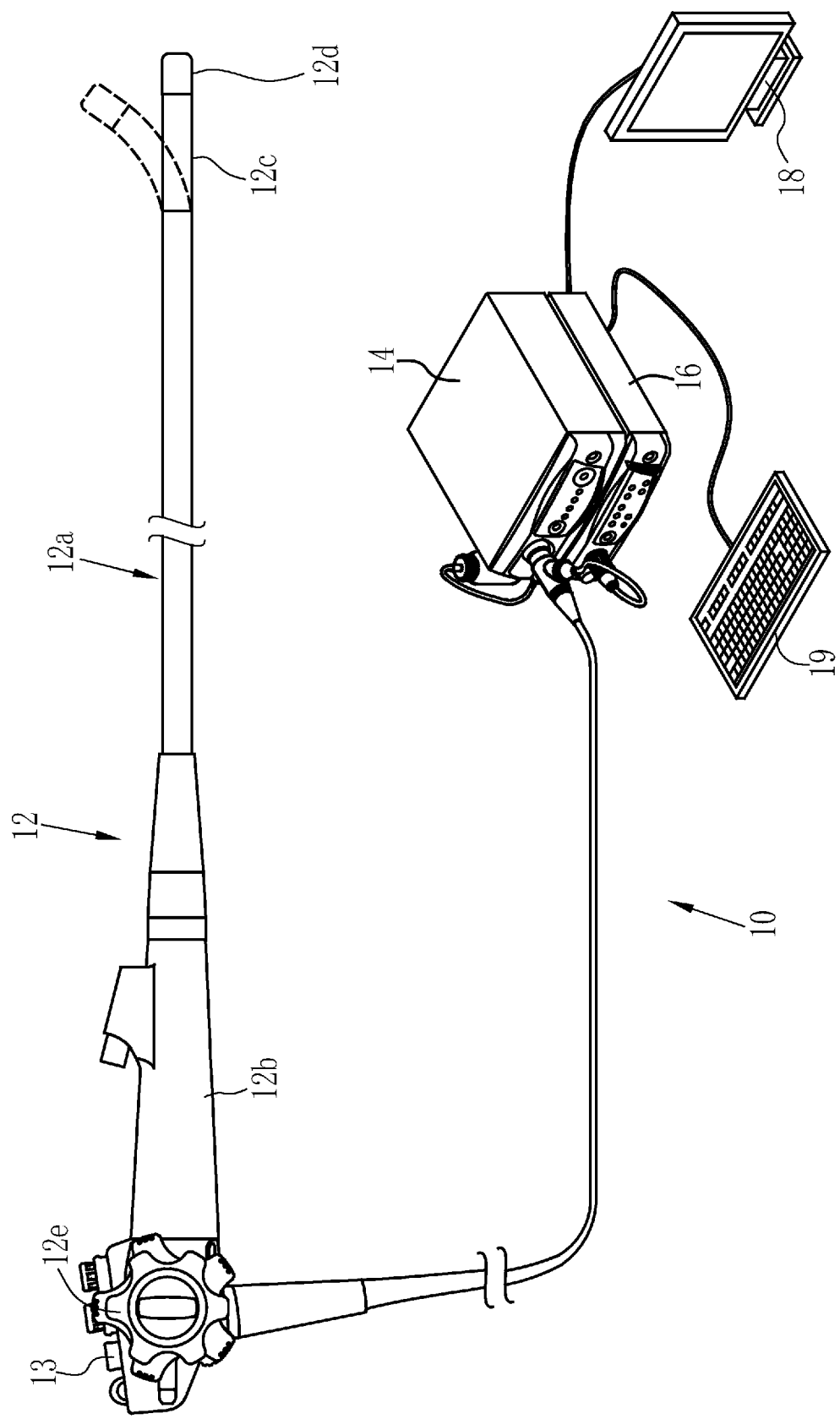
FIG. 1 is an external view of an endoscope system.

As illustrated in FIG. 1, an endoscope system 10 (endoscope device) includes an endoscope 12, a light source device 14, a processor device 16, a monitor 18, and a console 19. The endoscope 12 photographs a photographic subject. The light source device 14 generates illumination light. The processor device 16 performs system control, image processing, and the like for the endoscope system 10. The monitor 18 is a display unit that displays an image captured by the endoscope 12 (endoscope image). The console 19 is an input device used for inputting settings to the processor device 16, for example.

The endoscope 12 has an insertion part 12a that is to be inserted into a subject, an operating unit 12b provided at the base end portion of the insertion part 12a, and a bending part 12c and a tip part 12d provided at the distal end side of the insertion part 12a. Operation of an angle knob 12e of the operating unit 12b causes the bending part 12c to bend. As a result, the tip part 12d is oriented in a desired direction. In addition, the operating unit 12b is provided with a zoom operating unit 13 in addition to the angle knob 12e. Operation of the zoom operating unit 13 causes zoom in or zoom out of the photographic subject for image capturing.

Figure 2:
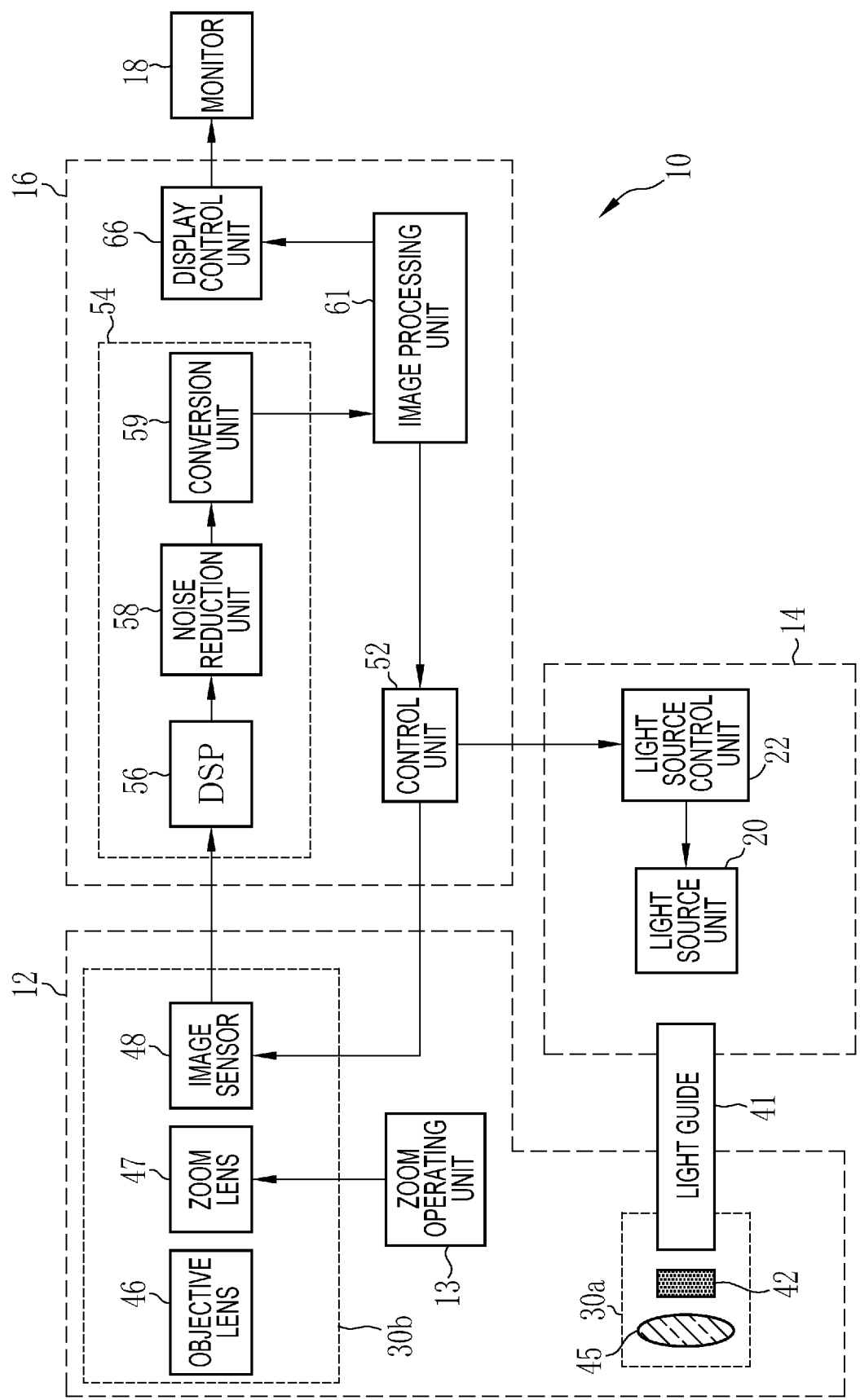
FIG. 2 is a block diagram of the endoscope system.

As illustrated in FIG. 2, the light source device 14 includes a light source unit 20 that emits illumination light and a light source control unit 22 that controls operation of the light source unit 20.

The light source unit 20 emits illumination light to illuminate the photographic subject, excitation light to be used for emitting illumination light, or the like. The light source unit 20 includes, for example, a light source such as a laser diode (hereinafter referred to as LD), a light emitting diode (LED), a xenon lamp, or a halogen lamp and at least emits white illumination light or excitation light to be used for emitting white illumination light. The white color includes so-called pseudo white, which is substantially the same as white in photographing a photographic subject by using the endoscope 12. The light source unit 20 includes, as necessary, a fluorescent body that emits light by being irradiated with excitation light, an optical filter that adjusts the wavelength range, spectrum, light amount, or the like of the illumination light or excitation light, and the like. Besides, the light source unit 20 can emit light having a specific wavelength range that is necessary to capture an image to be used for calculating biological information such as the oxygen saturation of hemoglobin included in the photographic subject.

In this embodiment, the light source unit 20 includes a first laser diode (LD) that emits first excitation light with a center wavelength of about 473 nm and a second LD that emits second excitation light with a center wavelength of about 445 nm. Illumination light emitted from the light source unit 20 enters a light guide 41. The light guide 41 is incorporated in the endoscope 12 and a universal cord, and the illumination light propagates therethrough to the tip part 12d of the endoscope 12. The universal cord is a cord connecting the endoscope 12, the light source device 14, and the processor device 16.

The light source control unit 22 controls timings for turning on, turning off, or shielding the respective light sources that constitute the light source unit 20, light emission amounts thereof, and the like. As a result, the light source unit 20 can emit a plurality of kinds of illumination light with different spectra. In addition, the light source control unit 22 controls the light source unit 20 in accordance with a photographing timing (so-called frame).

The tip part 12d of the endoscope 12 is provided with an illumination optical system 30a and an imaging optical system 30b. The illumination optical system 30a has an illumination lens 45, and illumination light is emitted toward the photographic subject through the illumination lens 45. In this embodiment, the illumination optical system 30a has, in addition to the illumination lens 45, a fluorescent body 42 that emits light by being irradiated with the first excitation light or the second excitation light. The fluorescent body 42 transmits part of the first excitation light or the second excitation light and emits generally green to red fluorescence. Thus, the illumination optical system 30a generally emits white illumination light, which are the first excitation light or the second excitation light transmitted through the fluorescent body 42 and fluorescence emitted from the fluorescent body 42, toward the photographic subject. Hereinafter, white illumination light emitted in a case of using the first excitation light will be referred to as first white light W1, and white illumination light emitted in a case of using the second excitation light will be referred to as second white light W2. In addition, light of a blue component included in the first white light W1, light of a green component included in the first white light W1, and light of a red component included in the first white light W1 will be respectively referred to as blue light B1, green light G1, and red light RE Light of a blue component included in the second white light W2, light of a green component included in the second white light W2, and light of a red component included in the second white light W2 will be respectively referred to as blue light B2, green light G2, and red light R2.

The imaging optical system 30b has an objective lens 46, a zoom lens 47, and an image sensor 48. The image sensor 48 photographs the photographic subject by using, for example, reflected light (including, in addition to reflected light, scattered light, fluorescence emitted from the photographic subject, fluorescence caused by medicine that is, for example, administered to the photographic subject, and the like) of illumination light returning from the photographic subject through the objective lens 46 and the zoom lens 47. The zoom lens 47 is moved by operating the zoom operating unit 13 and zooms in or zooms out the photographic subject to be photographed by the image sensor 48.

The image sensor 48 is, for example, a color sensor having color filters of the primary color system and includes three types of pixels, which are a B pixel (blue pixel) having a blue color filter, a G pixel (green pixel) having a green color filter, and an R pixel (red pixel) having a red color filter. The blue color filter mainly transmits violet to blue light. The green color filter mainly transmits green light. The red color filter mainly transmits red light. Thus, at single-time image capturing, three types of images, which are a B image (blue image), a G image (green image), and an R image (red image), can be obtained concurrently.

A charge coupled device (CCD) sensor or a complementary metal oxide semiconductor (CMOS) sensor can be used as the image sensor 48. In addition, although the image sensor 48 according to this embodiment is a color sensor of the primary color system, a color sensor of the complementary color system can also be used. The color sensor of the complementary color system has, for example, a cyan pixel provided with a cyan color filter, a magenta pixel provided with a magenta color filter, a yellow pixel provided with a yellow color filter, and a green pixel provided with a green color filter. Images obtained from the pixels of the above respective colors when using the color sensor of the complementary color system can be converted into a B image, a G image, and an R image through complementary color-to-primary color conversion. In addition, instead of the color sensor, a monochrome sensor without a color filter can be used as the image sensor 48. In this case, by sequentially photographing the photographic subject by using illumination light of the respective colors such as BGR, images of the above respective colors can be obtained.

The processor device 16 has a control unit 52, an image acquiring unit 54, an image processing unit 61, and a display control unit 66 (see FIG. 2).

The control unit 52 performs general control of the endoscope system 10 such as synchronization control of an illumination-light irradiation timing and a photographing timing. In addition, if various settings are input by using the console 19 or the like, for example, the control unit 52 inputs the settings to the units of the endoscope system 10 such as the light source control unit 22, the image sensor 48, and the image processing unit 61.

The image acquiring unit 54 acquires a plurality of types of images obtained by photographing the photographic subject by using illumination light having different wavelength ranges. Specifically, the image acquiring unit 54 acquires a first frame image obtained by photographing the photographic subject and a second frame image obtained by photographing the photographic subject at a timing different from that of the first frame image. Accordingly, the image acquiring unit 54 acquires images necessary to calculate specific biological information. The specific biological information is an oxygen saturation, a blood vessel depth, a blood vessel density, or other information obtained through arithmetic processing using an image obtained by photographing the photographic subject. In this embodiment, the specific biological information is an oxygen saturation.

Figures 3, 4:
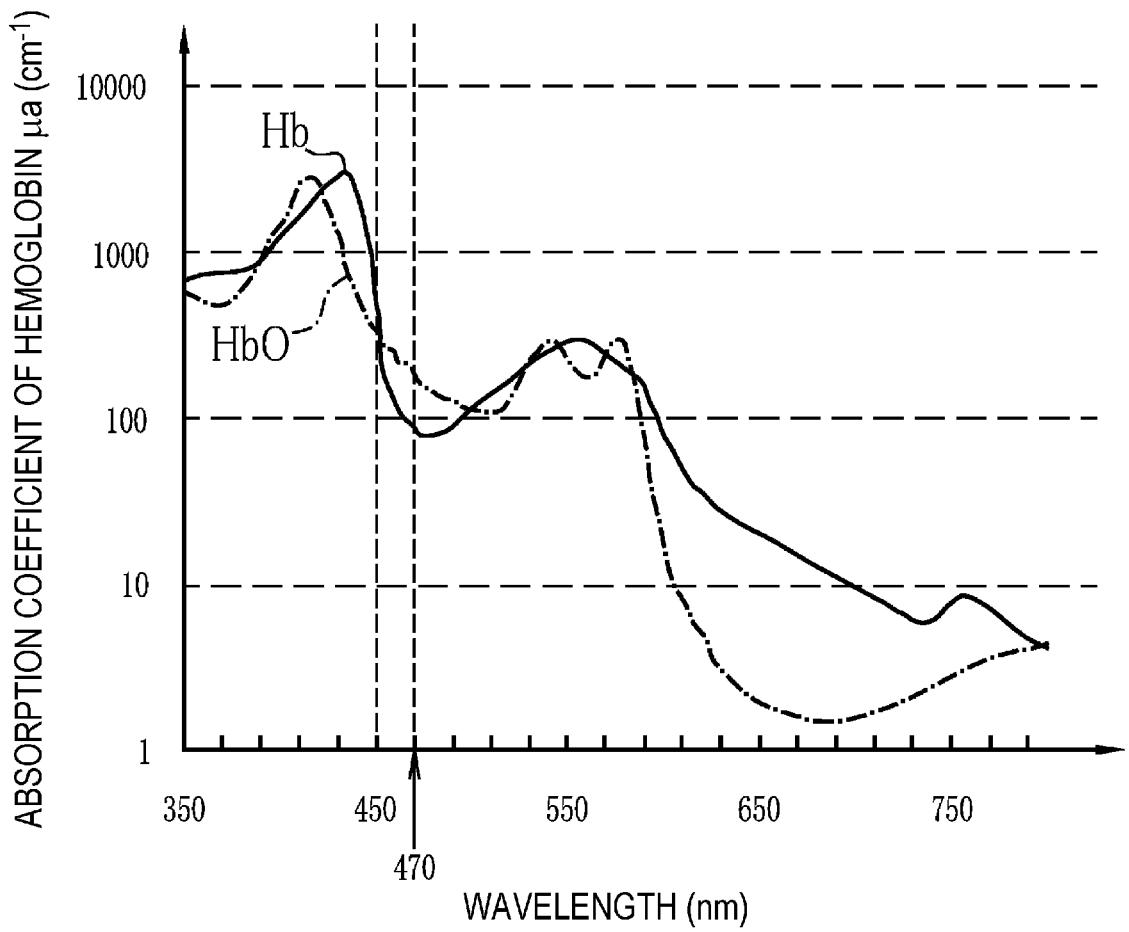
FIG. 3 is a table illustrating illumination light and an acquired image in each photographing frame.
FIG. 4 is a graph illustrating absorption coefficients of hemoglobin and oxidized hemoglobin.

More specifically, since the image sensor 48 has the color filters, the image acquiring unit 54 acquires an image for each illumination light and for each color filter. That is, as illustrated in FIG. 3, by photographing the photographic subject by using the first white light W1, an image of BGR colors is acquired, and by photographing the photographic subject by using the second white light W2, an image of BGR colors is acquired. In this embodiment, among a series of images obtained by photographing the photographic subject, an image obtained by photographing the photographic subject by using the first white light W1 is referred to as "first frame image", and an image obtained by photographing the photographic subject at a timing different from that of the first frame image is referred to as "second frame image". The second frame image is, for example, an image captured after (or before) photography for the first frame image. The first frame image and the second frame image are not necessarily successively captured images. However, to reduce the influence of a movement, if any, as much as possible, the first frame image and the second frame image in this embodiment are successively captured images, and the second frame image is captured after the first frame image. To successively capture the first frame image and the second frame image means to capture the first frame image and then capture the second frame image, or to capture the second frame image and then capture the first frame image, without capturing another image between the first frame image and the second frame image.

In capturing each of the first frame image and the second frame image, the image acquiring unit 54 acquires a B image, a G image, and an R image. However, different illumination light is used for capturing the first frame image and the second frame image. Thus, for distinction, the B image, the G image, and the R image acquired in capturing the first frame image are hereinafter referred to as a B1 image, a G1 image, and an R1 image, respectively, and similarly, the B image, the G image, and the R image acquired in capturing the second frame image are hereinafter referred to as a B2 image, a G2 image, and an R2 image, respectively. The B1 image, the G1 image, and the R1 image are each the first frame image, and the B2 image, the G2 image, and the R2 image are each the second frame image.

The blue light B1 included in the first white light W1 includes a large amount of the first excitation light, and at the center wavelength of the first excitation light, which is about 473 nm, the absorption coefficient of oxidized hemoglobin (HbO) and the absorption coefficient of reduced hemoglobin (Hb) have almost the maximum difference in the blue wavelength range as illustrated in FIG. 4. The blue light B2 included in the second white light W2 includes a large amount of the second excitation light, and at the center wavelength of the second excitation light, which is about 445 nm, the absorption coefficient of oxidized hemoglobin and the absorption coefficient of reduced hemoglobin have almost no difference. In addition, even if the excitation light differs to be the first excitation light and the second excitation light, the difference in the spectrum of fluorescence emitted by the fluorescent body 42 is small. Furthermore, compared with the blue light B1 included in the first white light W1, the green light G1 and the red light R1 included in the first white light W1 and the green light G2 and the red light R2 included in the second white light W2 have almost no difference in the absorption coefficient in accordance with the oxygen saturation. Therefore, the blue light B1 included in the first white light W1 is illumination light whose absorption coefficient changes in accordance with the oxygen saturation and the blue light B2 included in the second white light W2 is illumination light whose change in the absorption coefficient in accordance with the oxygen saturation is small compared with the blue light B1.

The image acquiring unit 54 has a digital signal processor (DSP) 56, a noise reduction unit 58, and a conversion unit 59, and performs various kinds of processing on the acquired images by using these units, as necessary.

The DSP 56 performs various kinds of processing on the acquired images, such as defect correction processing, offset processing, gain correction processing, linear matrix processing, gamma conversion processing, demosaicing processing, and YC conversion processing, as necessary.

The defect correction processing is processing for correcting the pixel value of a pixel corresponding to a defective pixel of the image sensor 48. The offset processing is processing for setting an accurate zero level by reducing a dark current component from an image subjected to the defect correction processing. The gain correction processing is processing for adjusting the signal level of each image by multiplying the image subjected to the offset processing by a gain. The linear matrix processing is processing for increasing the color reproducibility of an image subjected to the offset processing, and the gamma conversion processing is processing for adjusting the brightness and saturation of an image subjected to the linear matrix processing. The demosaicing processing (also referred to as isotropic processing or synchronization processing) is processing for interpolating the pixel value of a lacking pixel and is performed on an image subjected to the gamma conversion processing. The lacking pixel is a pixel without a pixel value due to the array of the color filters (because a pixel of another color is arranged in the image sensor 48). For example, in the demosaicing processing, pixel values of B pixels at positions of a G pixel and an R pixel are generated by interpolation using pixel values of B pixels. The same applies to the other colors. The YC conversion processing is processing for converting an image subjected to the demosaicing processing into a luminance channel Y, a chroma channel Cb, and a chroma channel Cr.

The noise reduction unit 58 performs noise reduction processing on the luminance channel Y, the chroma channel Cb, and the chroma channel Cr, by using, for example, a moving average method, a median filter method, or the like. The conversion unit 59 re-converts the luminance channel Y, the chroma channel Cb, and the chroma channel Cr, which have been subjected to the noise reduction processing, into images of BGR colors again.

Figure 5:
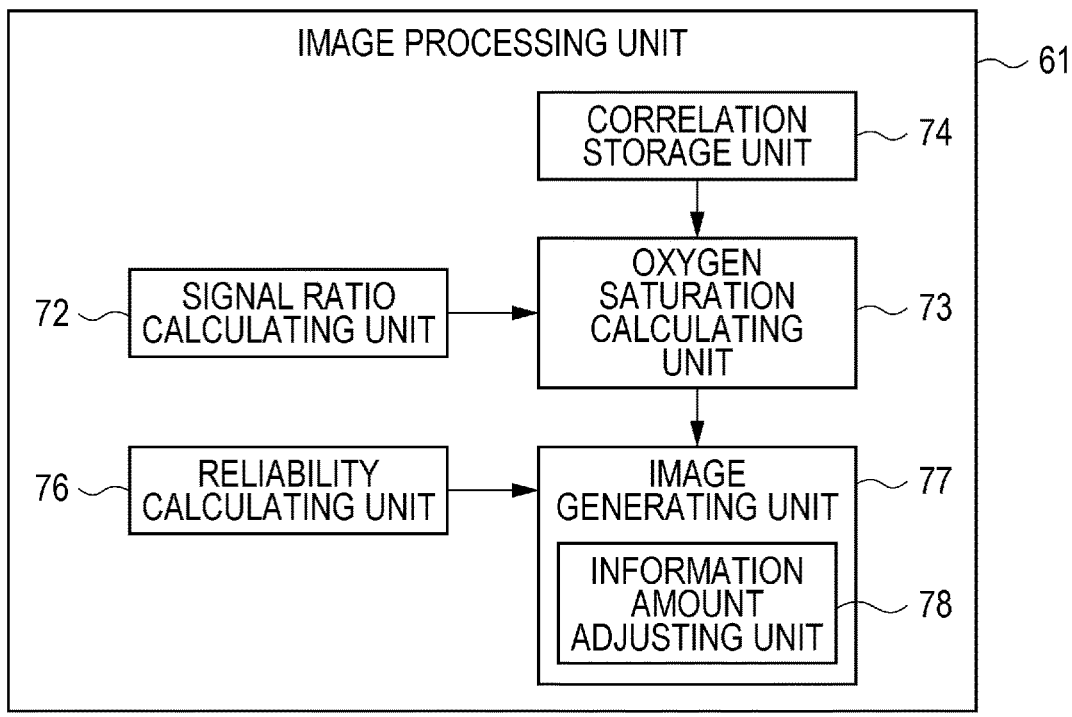
FIG. 5 is a block diagram illustrating a configuration of an image processing unit.

The image processing unit 61 generates an image to be displayed by using the images acquired by the image acquiring unit 54. In this embodiment, the image processing unit 61 calculates an oxygen saturation by using the images acquired by the image acquiring unit 54 and generates, as the image to be displayed, an oxygen saturation image representing the oxygen saturation. As illustrated in FIG. 5, the image processing unit 61 includes a signal ratio calculating unit 72, an oxygen saturation calculating unit 73, a correlation storage unit 74, a reliability calculating unit 76, and an image generating unit 77.

The signal ratio calculating unit 72 calculates a signal ratio to be used by the oxygen saturation calculating unit 73 to calculate the oxygen saturation. Specifically, the signal ratio calculating unit 72 calculates a signal ratio "B1/G2", which is a ratio of the pixel value of the B1 image to the pixel value of the G2 image and a signal ratio "R2/G2", which is a ratio of the pixel value of the R2 image to the pixel value of the G2 image. The value of R1/G2 depends on the oxygen saturation and a blood amount (blood concentration), and the value of R2/G2 depends on the blood amount. Note that each signal ratio calculated by the signal ratio calculating unit 72 is calculated for each pixel or each unit if a plurality of pixels are set as a unit.

Figure 6:
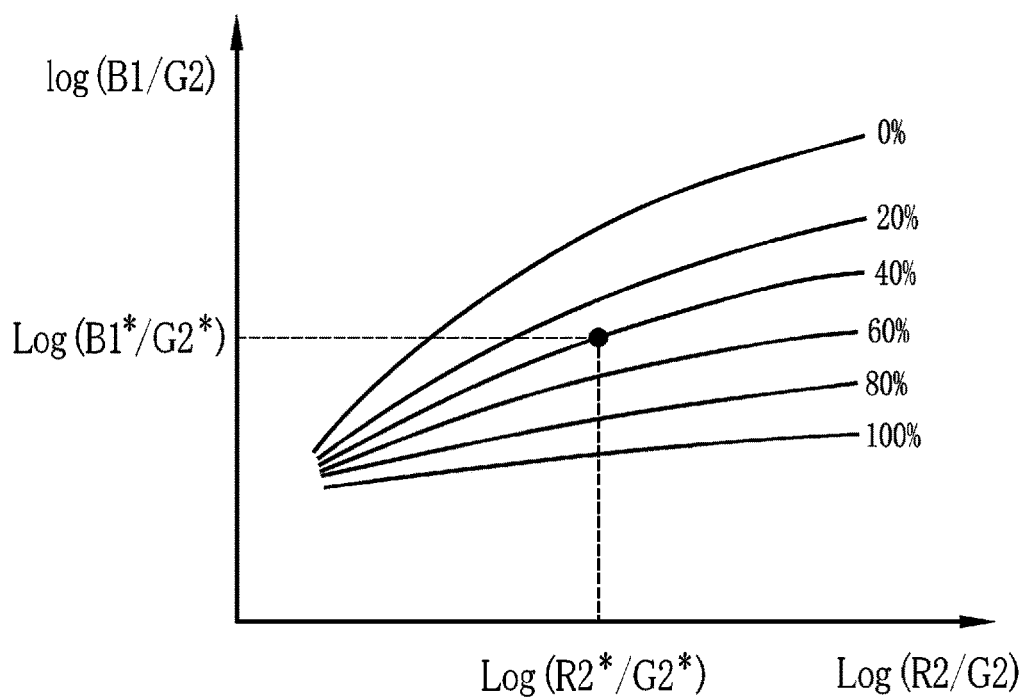
FIG. 6 is a graph illustrating a correlation between ratios of pixel values and an oxygen saturation.

The oxygen saturation calculating unit 73 calculates the oxygen saturation by using a signal ratio calculated by the signal ratio calculating unit 72 and a correlation stored in the correlation storage unit 74. As illustrated in FIG. 6, the correlation stored in the correlation storage unit 74 associates, for example, the log of B1/G2 (log(B1/G2)) and the log of R2/G2 (log(R2/G2)) with oxygen saturation values. By referring to this correlation, the oxygen saturation calculating unit 73 can calculate the oxygen saturation by excluding the influence of the blood amount. For example, at a specific pixel, if the value of B1/G2 is "B1*/G2*" and the value of R2/G2 is "R2*/G2*", the oxygen saturation calculating unit 73 calculates the oxygen saturation at this specific pixel as "40%". Note that the oxygen saturation calculating unit 73 calculates the oxygen saturation for each pixel or each unit if a plurality of pixels are set as a unit.

The reliability calculating unit 76 calculates "reliability" representing the accuracy of the oxygen saturation calculated by the oxygen saturation calculating unit 73. The reliability calculating unit 76 uses, in calculating reliability that is to be finally output (hereinafter referred to as reliability Z), at least a signal ratio that is a ratio between a "pixel value in a first specific wavelength range corresponding to a specific wavelength range of the first frame image" and a "pixel value in a second specific wavelength range corresponding to the specific wavelength range of the second frame image". The reliability calculated by the reliability calculating unit 76 is calculated for each pixel or each unit if a plurality of pixels are set as a unit, in the same manner as the unit for calculating the oxygen saturation.

In this embodiment, the "pixel value in a first specific wavelength range corresponding to a specific wavelength range of the first frame image" is the pixel value of the G1 image, and the "pixel value in a second specific wavelength range corresponding to the specific wavelength range of the second frame image" is the pixel value of the G2 image. Thus, the reliability calculating unit 76 calculates a signal ratio "G1/G2" (or G2/G1), which is a ratio between the pixel value of the G1 image and the pixel value of the G2 image and calculates first reliability Y1 by using the calculated G1/G2.

The pixel in the first specific wavelength range and the pixel in the second specific wavelength range are pixels of images obtained by photographing a photographic subject under the same conditions regarding the spectrum of the illumination light in the first frame pixel and the second frame pixel, respectively. Thus, G1/G2 is almost "1" (specific value Iv) if there is no movement of the photographic subject or no relative movement between the photographic subject and the endoscope 12 (hereinafter simply referred to as "movement"), or, if there is a movement, varies from this specific value depending on the magnitude of the movement. That is, G1/G2 represents the magnitude of the movement. In addition, the first reliability Y1 calculated by using G1/G2 represents the oxygen saturation calculation accuracy (accuracy) depending on the movement.

Figure 7:
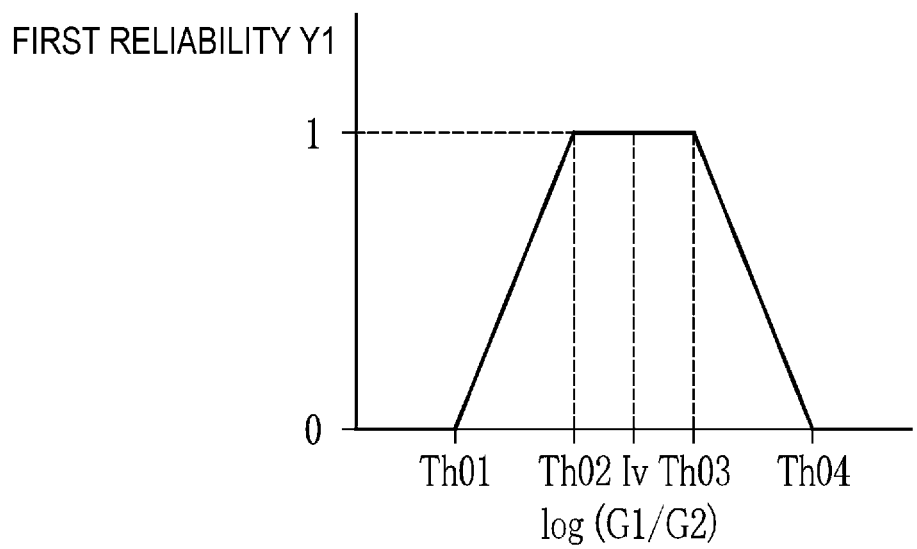
FIG. 7 is a graph of first reliability.

If there is a movement, the oxygen saturation calculation accuracy decreases. Thus, as illustrated in FIG. 7, the reliability calculating unit 76 calculates the first reliability Y1 by using G1/G2. That is, if the value of log(G1/G2) falls within a first specific range that includes the specific value Iv ("1") and is greater than or equal to a threshold value Th02 and less than or equal to a threshold value Th03, the first reliability Y1 is a constant value (e.g., "1"). In addition, if the value of log(G1/G2) falls out of the first specific range, the first reliability Y1 gradually decreases as the value of log(G1/G2) is more away from the specific value Iv. For example, if log(G1/G2) is less than the threshold value Th02, the first reliability Y1 gradually decreases as the value of log(G1/G2) is more away from the specific value Iv, and if log(G1/G2) is less than or equal to a threshold value Th01 (Th01<Th02), the first reliability Y1 equals to zero ("0"). In addition, if log(G1/G2) is greater than the threshold value Th03, the first reliability Y1 gradually decreases as the value of log(G1/G2) is more away from the specific value Iv, and if log(G1/G2) is greater than or equal to a threshold value Th04 (Th03<Th04), the first reliability Y1 equals to zero ("0").

Note that when the "pixel value in a first specific wavelength range corresponding to a specific wavelength range of the first frame image" is the pixel value of the R1 image, the "pixel value in a second specific wavelength range corresponding to the specific wavelength range of the second frame image" is the pixel value of the R2 image. In this case, the reliability calculating unit 76 calculates a signal ratio "R1/R2" (or "R2/R1"), which is a ratio between the pixel value of the R1 image and the pixel value of the R2 image and calculates first reliability Y1 by using the value of R1/G2. In addition, the "specific wavelength range" is, as described above, preferably a green wavelength range or a red wavelength range. Otherwise, the photographic subject is not assumed to be photographed under the same conditions regarding the spectrum of the illumination light because the blue light B1 and the blue light B2 have a great difference in the degree of change with respect to the absorption coefficient of hemoglobin in accordance with the oxygen saturation. Furthermore, although the first reliability Y1 is a parameter to be used for calculating the reliability Z to be finally output by the reliability calculating unit 76, the reliability calculating unit 76 can output the first reliability Y1 as the reliability Z.

In this embodiment, the reliability calculating unit 76 calculates the reliability Z to be finally output by using, in addition to G1/G2 above, the pixel value of the first frame image and the pixel value of the second frame image. Specifically, by using the pixel value of the first frame image and the pixel value of the second frame image, the reliability calculating unit 76 calculates second reliability Y2 to be used for calculating the reliability Z to be finally output.

Figure 8:
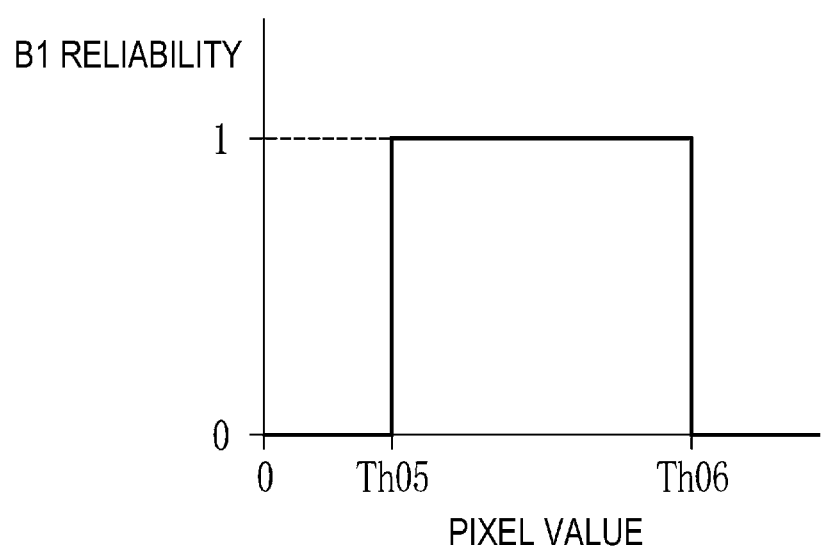
FIG. 8 is a graph of B1 reliability to be used for calculating second reliability.

Calculation of the second reliability Y2 uses, for example, B1 reliability, G1 reliability, R1 reliability, B2 reliability, G2 reliability, and R2 reliability. The B1 reliability is calculated by using the pixel value of the B1 image, which is the first frame image. The G1 reliability is calculated by using the pixel value of the G1 image, which is the first frame image. The R1 reliability is calculated by using the pixel value of the R1 image, which is the first frame image. The B2 reliability is calculated by using the pixel value of the B2 image, which is the second frame image. The G2 reliability is calculated by using the pixel value of the G2 image, which is the second frame image. The R2 reliability is calculated by using the pixel value of the R2 image, which is the second frame image. As illustrated in FIG. 8, if the pixel value of the B1 image falls within a second specific range that is greater than or equal to a threshold value Th05 and less than or equal to a threshold value Th06, the B1 reliability is a constant value "1". In addition, if the pixel value of the B1 image falls out of the second specific range (less than the threshold value Th05 or greater than the threshold value Th06), the B1 reliability equals to zero ("0"). The same applies to the G1 reliability, the R1 reliability, the B2 reliability, the G2 reliability, and the R2 reliability.

The reliability calculating unit 76 sets, as the second reliability Y2, for example, the minimum out of the B1 reliability, the G1 reliability, the R1 reliability, the B2 reliability, the G2 reliability, and the R2 reliability. Thus, if the pixel value of the first frame image and the pixel value of the second frame image fall within the second specific range, the second reliability Y2 is a constant value. In addition, if one or more of the pixel value of the first frame image and the pixel value of the second frame image fall out of the second specific range, the second reliability Y2 equals to zero. That is, if the pixel value in an image of any color that is the first frame image or an image of any color that is the second frame image corresponds to a halation part or a dark part, the second reliability Y2 is "0"; otherwise, the second reliability Y2 is "1". Note that the reliability calculating unit 76 in this embodiment calculates the second reliability Y2 by using all of acquired images of the respective colors of the first frame image and images of the respective colors of the second frame image; however, the second reliability Y2 may alternatively be calculated by using at least only an image to be used by the signal ratio calculating unit 72 and an image to be used by the reliability calculating unit 76 for arithmetic processing (e.g., calculation of the first reliability Y1) other than arithmetic processing for the second reliability Y2.

The reliability calculating unit 76 sets, as the reliability Z to be finally output, the minimum out of the first reliability Y1 and the second reliability Y2. Thus, the reliability Z represents the magnitude of the movement and whether there is a fault such as halation, which can be determined on the basis of the pixel value.

The image generating unit 77 generates, for example, a so-called white light image by using the B2 image, the G2 image, and the R2 image, which are each the second frame image. In addition, by coloring the white light image by using the oxygen saturation value calculated by the oxygen saturation calculating unit 73, an oxygen saturation image representing the oxygen saturation value by color is generated as an image to be displayed.

The image generating unit 77 has an information amount adjusting unit 78 that adjusts an information amount of the oxygen saturation by using the reliability Z when the oxygen saturation image is generated. The information amount adjusting unit 78 acquires the reliability Z from the reliability calculating unit 76 and multiplies a chroma channel image of the white light image by the reliability Z to generate a chroma channel image for an oxygen saturation image. The image generating unit 77 uses a luminance channel image of the white light image for the luminance channel Y and assigns, to the chroma channel Cr, Cr×Z obtained by multiplying the chroma channel image (Cr) of the white light image by the reliability and also assigns, to the chroma channel Cb, Cb×Z obtained by multiplying the chroma channel image (Cb) of the white light image by the reliability to generate an oxygen saturation image. Thus, the oxygen saturation image has color in accordance with the oxygen saturation value in a part where the reliability Z is high, but in a part where the reliability Z is low, the color approaches an achromatic color regardless of the oxygen saturation value, and the information amount of the oxygen saturation is small.

The display control unit 66 acquires the image to be displayed from the image generating unit 77 and converts the acquired image to a format that is suitable for display and outputs it to the monitor 18. Thus, the monitor 18 displays the oxygen saturation image in this embodiment.

Figure 9:
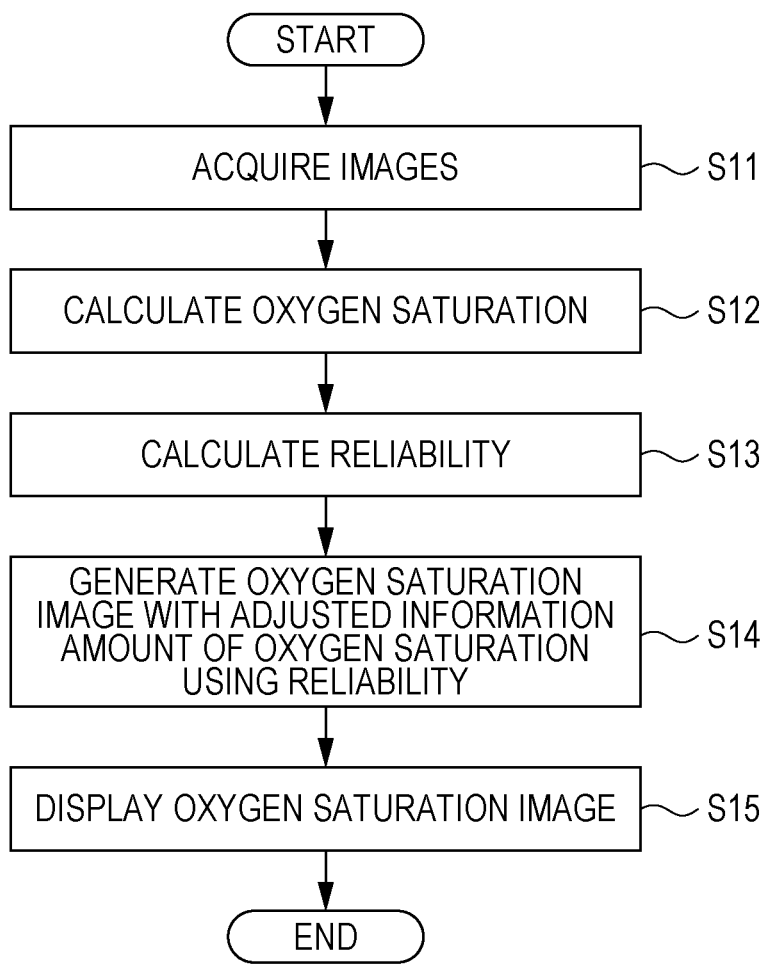
FIG. 9 is a flowchart illustrating flow of calculation of an oxygen saturation.

Now, a process flow to generate and display an oxygen saturation image in the endoscope system 10 will be described with reference to the flowchart illustrated in FIG. 9. First, by photographing a photographic subject while switching the illumination light between at least the first white light W1 and the second white light W2, the image acquiring unit 54 acquires images that are necessary to calculate the oxygen saturation and to generate an oxygen saturation image (step S11). That is, the image acquiring unit 54 acquires the B1 image, the G1 image, and the R1 image, each of which is the first frame image, in capturing the first frame image using the first white light W1 and acquires the B2 image, the G2 image, and the R2 image, each of which is the second frame image, in capturing the second frame image using the second white light W2.

Upon the image acquiring unit 54 acquiring the first frame image and the second frame image, the oxygen saturation is calculated by using these images (step S12). Specifically, the signal ratio calculating unit 72 calculates B1/G2 and R2/G2, and then the oxygen saturation calculating unit 73 calculates the oxygen saturation for each pixel by using B1/G2 and R2/G2 and the correlation stored in the correlation storage unit 74.

While the oxygen saturation is calculated in this manner, the reliability calculating unit 76 calculates the reliability Z reflecting the degree of reduction of the oxygen saturation calculation accuracy depending on a movement (step S13). Specifically, the reliability calculating unit 76 calculates the first reliability Y1 reflecting the magnitude of the movement by using G1/G2. In addition, the reliability calculating unit 76 calculates the second reliability Y2 reflecting whether there is a halation part or a dark part by using the pixel value of the first frame image and the pixel value of the second frame image. Then, the minimum out of the first reliability Y1 and the second reliability Y2 is set as the reliability Z.

When the oxygen saturation calculating unit 73 calculates the oxygen saturation and the reliability calculating unit 76 calculates the reliability Z, the image generating unit 77 generates the oxygen saturation image, which represents the oxygen saturation value by color, while the information amount adjusting unit 78 adjusts the information amount of the oxygen saturation by using the reliability Z (step S14). When the image generating unit 77 generates the oxygen saturation image, the monitor 18 displays the oxygen saturation image (step S15). In the oxygen saturation image in which the information amount of the oxygen saturation is adjusted by using the reliability Z, visibility of the oxygen saturation is high because a part where the reliability Z is high is displayed in color in accordance with the oxygen saturation value. Thus, the information amount of the oxygen saturation is large in the part where the reliability Z is high. On the other hand, since the color approaches an achromatic color regardless of the oxygen saturation value in a part where the reliability Z is low, the visibility of the oxygen saturation is low. As a result, the information amount of the oxygen saturation in the part where the reliability Z is low is relatively small compared with that in the part where the reliability Z is high.

As described above, the endoscope system 10 calculates the reliability Z reflecting at least the magnitude of the movement. In addition, since the oxygen saturation image is generated by adjusting the information amount of the oxygen saturation by using the reliability Z, even if there is a movement, the information amount of the oxygen saturation can be adjusted in accordance with the accuracy thereof.

The display color is changed in accordance with the reliability Z in this embodiment. Besides, if the oxygen saturation is displayed as a numeral, for the part where the reliability Z is low, it is also possible to display a small numeral (display a numeral in a relatively small size compared with the size of a numeral representing the part where the reliability Z is high) or not to display a numeral. In addition, the information amount is adjusted in display of the monitor in this embodiment. However, the adjustment of the information amount is not limited to this. For example, in a case where the oxygen saturation is not displayed on the monitor or the like, the information amount can be adjusted by substituting the oxygen saturation with a value with a weak relation with the oxygen saturation, such as "NULL", for the part where the reliability Z is low.

Second Embodiment

The reliability calculating unit 76 calculates the reliability Z to be finally output by using the first reliability Y1 and the second reliability Y2 in the above first embodiment. However, the reliability calculating unit 76 can also calculate the reliability Z by using, in addition to at least the first reliability Y1, a ratio between the pixel value of the first frame image and the pixel value of the second frame image corresponding to different wavelength ranges.

For example, the reliability calculating unit 76 can calculate the reliability Z by using a "second signal ratio" that is a ratio between the pixel value of the first frame image or the pixel value of the second frame image corresponding to the red wavelength range and the pixel value of the first frame image or the pixel value of the second frame image corresponding to the green wavelength range.

The "pixel value of the first frame image or the pixel value of the second frame image corresponding to the red wavelength range" is the pixel value of the R1 image or the pixel value of the R2 image. The "pixel value of the first frame image or the pixel value of the second frame image corresponding to the green wavelength range" is the pixel value of the G1 image or the pixel value of the G2 image. Thus, the "second signal ratio" is R1/G1 (or G1/R1), R1/G2 (or G2/R1), R2/G1 (or G1/R2), or R2/G2 (or G2/R2). These values of the "second signal ratio" all depend on the blood amount.

Figure 10:
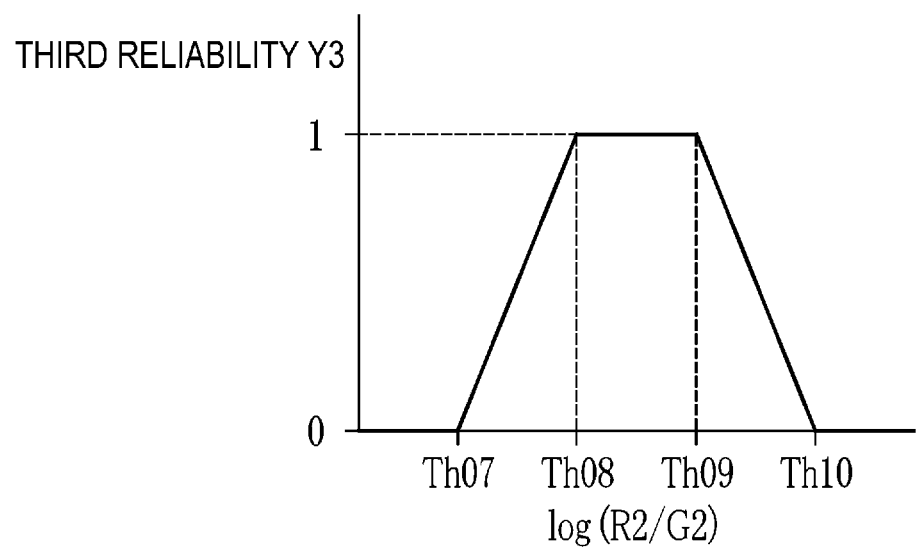
FIG. 10 is a graph of third reliability.

In this embodiment, in addition to the signal ratio (a first signal ratio) for calculating the first reliability Y1 and the like, the reliability calculating unit 76 further calculates R2/G2 as the second signal ratio and, as illustrated in FIG. 10, calculates third reliability Y3 by using R2/G2. That is, if the value of log(R2/G2) falls within a third specific range that is greater than or equal to a threshold value Th08 and less than or equal to a threshold value Th09, the third reliability Y3 is a constant value (e.g., "1"). In addition, if the value of log(R2/G2) falls out of the third specific range, the third reliability Y3 gradually decreases in accordance with the value of log(R2/G2). For example, if log(R2/G2) is less than the threshold value Th08, the third reliability Y3 gradually decreases, and if log(R2/G2) is less than or equal to a threshold value Th07 (Th07<Th08), the third reliability Y3 equals to zero ("0"). In addition, if log(R2/G2) is greater than the threshold value Th09, the third reliability Y3 gradually decreases, and if log(R2/G2) is greater than or equal to a threshold value Th10 (Th09<Th10), the third reliability Y3 equals to zero ("0"). The reliability calculating unit 76 sets, as the reliability Z to be finally output, the minimum out of the first reliability Y1, the second reliability Y2, and the third reliability Y3. In a case where the second reliability Y2 is not calculated, the minimum out of the first reliability Y1 and the third reliability Y3 is set as the reliability Z to be finally output.

If the third reliability Y3 calculated by using the second signal ratio that depends on the blood amount is used for calculating the reliability Z as above, a large information amount of the oxygen saturation can be maintained for a part where the blood amount is appropriate, and the information amount of the oxygen saturation can be decreased for a part where the blood amount is not appropriate and the accuracy of the calculated oxygen saturation is low by making color close to an achromatic color. As a result, for example, even in a case where the photographic subject bleeds, the information amount of the oxygen saturation can be adjusted in accordance with the accuracy thereof.

Third Embodiment

In addition to the above, for example, the reliability calculating unit 76 can calculate the reliability Z by using a "third signal ratio" that is a ratio between the pixel value of the first frame image or the pixel value of the second frame image corresponding to the blue wavelength range and the pixel value of the first frame image or the pixel value of the second frame image corresponding to the green wavelength range.

The "pixel value of the first frame image or the pixel value of the second frame image corresponding to the blue wavelength range" is the pixel value of the B1 image or the pixel value of the B2 image. The "pixel value of the first frame image or the pixel value of the second frame image corresponding to the green wavelength range" is the pixel value of the G1 image or the pixel value of the G2 image. Thus, the "third signal ratio" is B1/G1 (or G1/B1), B1/G2 (or G2/B1), B2/G1 (or G1/B2), or B2/G2 (or G2/B2). These values of the "third signal ratio" all depend on whether there is a residue including a yellow pigment, such as bilirubin, and an attachment amount thereof.

Figure 11:
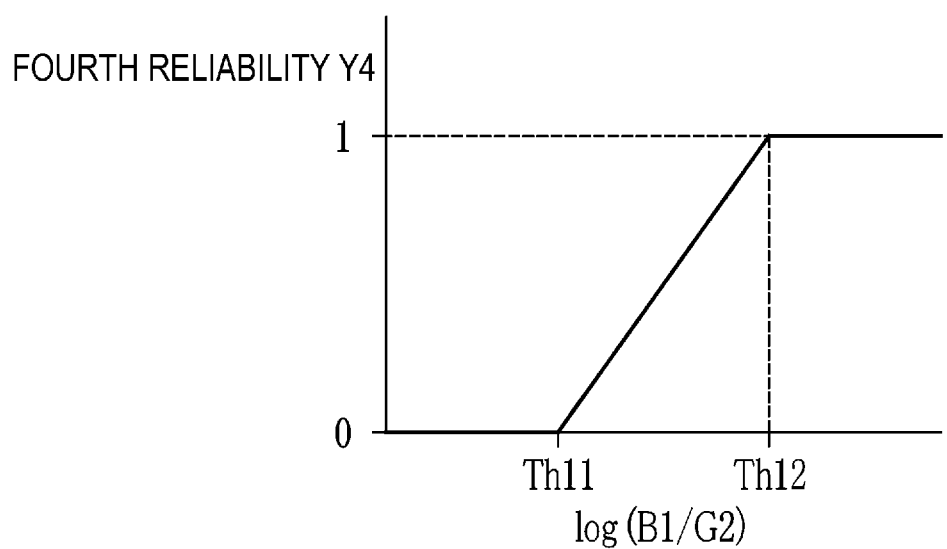
FIG. 11 is a graph of fourth reliability.

In this embodiment, in addition to the signal ratio (the first signal ratio) for calculating the first reliability Y1 and the like, the reliability calculating unit 76 further calculates B1/G2 as the third signal ratio and, as illustrated in FIG. 11, calculates fourth reliability Y4 by using B1/G2. That is, if the value of log(B1/G2) is less than or equal to a threshold value Th11 and the attachment amount of the residue or the like is large, the fourth reliability Y4 is zero ("0"). In addition, if the value of log(B1/G2) is greater than or equal to the threshold Th12 (Th11<Th12) and the attachment amount of the residue or the like is small, the fourth reliability Y4 is a constant value ("1"). Furthermore, if the value of log(B1/G2) falls within a range that is greater than the threshold Th11 and less than the threshold Th12, the fourth reliability Y4 gradually decreases as the third signal ratio is smaller.

The reliability calculating unit 76 sets, as the reliability Z to be finally output, the minimum out of the first reliability Y1, the second reliability Y2, the third reliability Y3, and the fourth reliability Y4. The same applies to a case where the second reliability Y2 is not calculated or a case where the third reliability Y3 is not calculated.

If the fourth reliability Y4 calculated by using the third signal ratio that depends on whether there is a residue or the like and an attachment amount thereof is used for calculating the reliability Z as above, a large information amount of the oxygen saturation can be maintained for a part where the attachment amount of the residue or the like is small, and the information amount of the oxygen saturation can be decreased for a part where the attachment amount of the residue or the like is large and the accuracy of the calculated oxygen saturation is low by making color close to an achromatic color. As a result, for example, even in a case where the residue or the like is attached to a portion or all of the photographic subject, the information amount of the oxygen saturation can be adjusted in accordance with the accuracy thereof.

Figure 12:
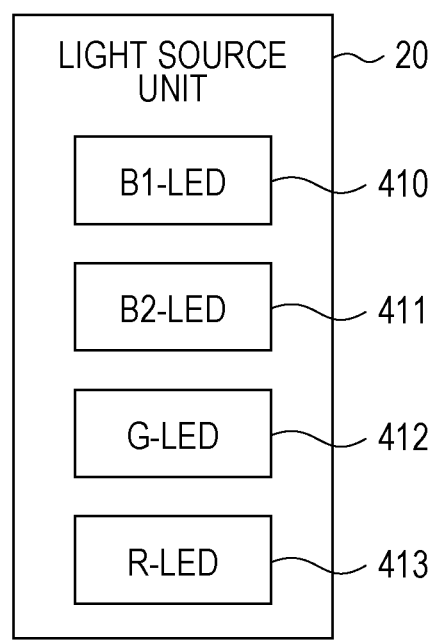
FIG. 12 is a block diagram illustrating a configuration of a light source unit according to a modification.

Note that, in the above first embodiment, the second embodiment, and the third embodiment, the light source unit 20 includes the first LD and the second LD, and the illumination light is generated by using these and the fluorescent body 42. However, the light source unit 20 may be constituted by LEDs. In this case, as illustrated in FIG. 12, the light source unit 20 includes a B1-LED 410 that emits blue light B1 with a center wavelength of about 470 nm, a B2-LED 411 that emits blue light B2 with a center wavelength of about 450 nm, a G-LED 412 that emits green light G with a center wavelength of about 540 nm, and an R-LED 413 that emits red light R with a center wavelength of about 650 nm. In addition, in capturing the first frame image, the photographic subject is photographed by using illumination light including the blue light B1, the green light G, and the red light R, and as a result, the image acquiring unit 54 can acquire a B1 image, a G1 image, and an R1 image. In capturing the second frame image, the photographic subject is photographed by using illumination light including the blue light B2, the green light G, and the red light R, and as a result, the image acquiring unit 54 can acquire a B2 image, a G2 image, and an R2 image.

Note that, in the above embodiments and the like, the oxygen saturation is calculated. However, the present invention is also useful when generating an image or the like representing other biological information (e.g., an image of a blood amount or a blood vessel at a specific depth). In a case where the other biological information is explicitly calculated, the oxygen saturation calculating unit 73 is a biological information calculating unit. In addition, in a case of generating an image representing the other biological information as a result, the oxygen saturation calculating unit 73 can be an arithmetic unit that performs necessary arithmetic processing by using a signal ratio in order to generate the image.

Figure 13:
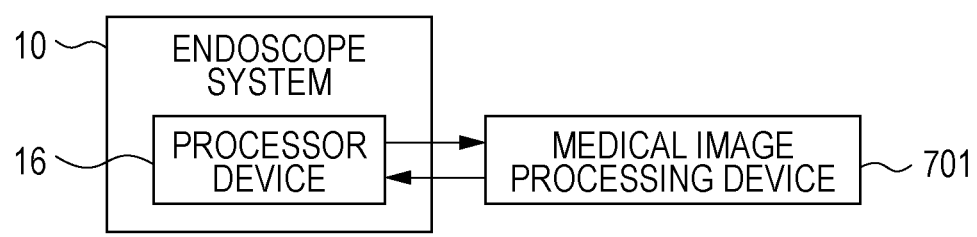
FIG. 13 is an explanatory diagram illustrating a relation between the endoscope system and an image processing device.
Figure 14:
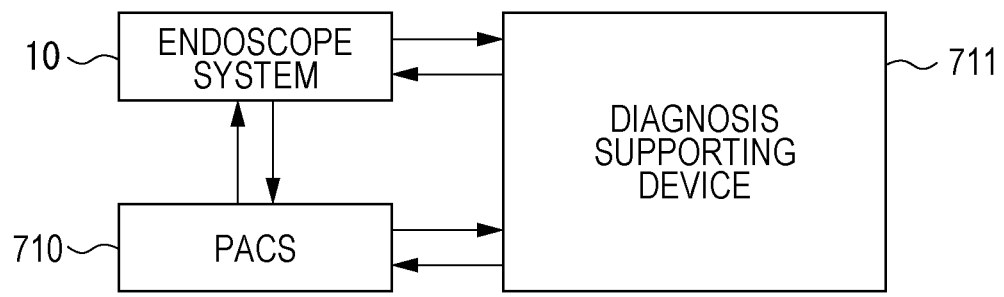
FIG. 14 is an explanatory diagram illustrating a relation among the endoscope system, a picture archiving and communication system (PACS), and a diagnosis supporting device.
Figure 15:
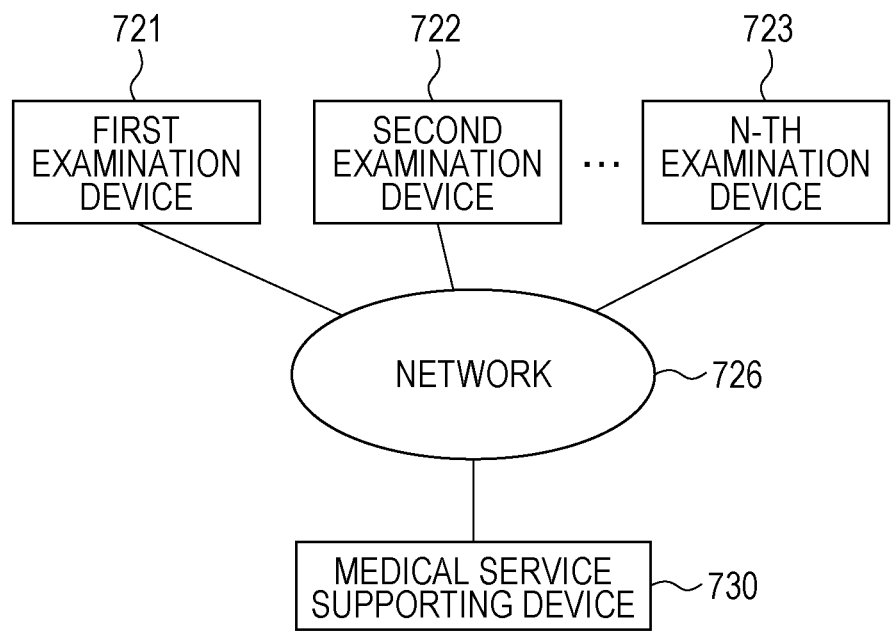
FIG. 15 is an explanatory diagram illustrating a relation among various examination devices and a medical service supporting device.

Besides, as illustrated in FIG. 13, some or all of the units constituting the image processing unit 61 of the endoscope system 10 can be provided in, for example, a medical image processing device 701 that works in collaboration with the endoscope system 10 by communicating with the processor device 16. In addition, as illustrated in FIG. 14, some or all of the units constituting the image processing unit 61 of the endoscope system 10 can be provided in, for example, a diagnosis supporting device 711 that acquires, directly from the endoscope system 10 or indirectly from a picture archiving and communication systems (PACS) 710, images captured by the endoscope 12. Furthermore, as illustrated in FIG. 15, some or all of the units constituting the image processing unit 61 of the endoscope system 10 can be provided in a medical service supporting device 730 that connects various examination devices such as a first examination device 721, a second examination device 722, ..., and an N-th examination device 723 including the endoscope system 10 via a network 726.

In the above embodiment, a hardware configuration of processing units that perform various kinds of processing, such as the light source control unit 22, the control unit 52, the image acquiring unit 54, each unit constituting the image acquiring unit 54, the image processing unit 61, each unit constituting the image processing unit 61, and the display control unit 66, is any of the following various processors. Various processors include a central processing unit (CPU) and a graphical processing unit (GPU) that are general-purpose processors functioning as various processing units by executing software (programs), a programmable logic device (PLD) that is a processor in which the circuit configuration is changeable after manufacture, such as field programmable gate array (FPGA), a dedicated electric circuit that is a processor having a circuit configuration that is specially designed to execute various kinds of processing.

One processing unit may be constituted by one of these various processors, or may be constituted by two or more processors of the same type or different types in combination (e.g., a combination of a plurality of FPGAs, a combination of a CPU and an FPGA, or a combination of a CPU and a GPU). In addition, a plurality of processing units may be configured from one processor. As a first example for constituting a plurality of processing units with one processor, one processor may be constituted by a combination of one or more CPUs and software, and this processor may function as a plurality of processing units, as typified by a computer such as a client or a server. As a second example, a processor may be used that implements the functions of the entire system including a plurality of processing units with one integrated circuit (IC) chip, as typified by a system on chip (SoC) or the like. In this manner, various processing units are constituted by one or more of the above various processors in terms of hardware configuration.

More specifically, the hardware configuration of these various processors is electric circuitry constituted by combining circuit elements such as semiconductor elements.

REFERENCE SIGNS LIST

10 endoscope system
12 endoscope
12*a* insertion part
12*b* operating unit
12*c* bending part
12*d* tip part
12*e* angle knob
13 zoom operating unit
14 light source device
16 processor device
18 monitor
19 console
20 light source unit
22 light source control unit
30*a* illumination optical system
30*b* imaging optical system
41 light guide
42 fluorescent body
45 illumination lens
46 objective lens
47 zoom lens
48 image sensor
52 control unit
54 image acquiring unit
56 digital signal processor (DSP)
58 noise reduction unit
59 conversion unit
61 image processing unit
66 display control unit
72 signal ratio calculating unit
73 oxygen saturation calculating unit
74 correlation storage unit
76 reliability calculating unit
77 image generating unit
78 information amount adjusting unit
410 B1-LED
411 B2-LED
412 G-LED
413 R-LED
701 medical image processing device
710 PACS
711 diagnosis supporting device
721 first examination device
722 second examination device
723 examination device
726 network
730 medical service supporting device
Iv specific value
Th01, Th02, Th03, Th04, Th05, Th06, Th07, Th08, Th09, Th10, Th11, Th12 threshold value
Y1 first reliability
Y2 second reliability
Y3 third reliability
Y4 fourth reliability
Z reliability
B1, B2 blue light
Cb chroma channel
Cr chroma channel
G, G1, G2 green light
Hb reduced hemoglobin
HbO oxidized hemoglobin
R, R1, R2 red light
S11, S12, S13, S14, S15 step
W1 first white light
W2 second white light

What is claimed is:
1. An endoscope system comprising:
a processor configured to function as:
an image acquiring unit that acquires a first frame image obtained by photographing a photographic subject and a second frame image obtained by photographing the photographic subject at a timing different from that of the first frame image;
an oxygen saturation calculating unit that calculates an oxygen saturation by using the first frame image and the second frame image;
a reliability calculating unit that calculates reliability of the oxygen saturation, calculated by the oxygen calculating unit, by using a signal ratio that is a ratio between a pixel value in a first specific wavelength range corresponding to a specific wavelength range of the first frame image and a pixel value in a second specific wavelength range corresponding to the specific wavelength range of the second frame image; and
an information amount adjusting unit that adjusts an information amount of the oxygen saturation by using the reliability, wherein the reliability calculating unit calculates the reliability by using the signal ratio, a pixel value of the first frame image, and a pixel value of the second frame image, wherein the reliability calculating unit calculates first reliability by using the signal ratio, calculates second reliability by using the pixel value of the first frame image and the pixel value of the second frame image, and outputs, as the reliability, a minimum out of the first reliability and the second reliability, and wherein the first reliability
- is a constant value if a value of the signal ratio falls within a first specific range including a specific value and
- gradually decreases as the value of the signal ratio is more away from the specific value if the value of the signal ratio falls out of the first specific range.

2. The endoscope system according to claim 1,
wherein the second reliability
- is a constant value if the pixel value of the first frame image and the pixel value of the second frame image fall within a second specific range and
- is zero if one or more of the pixel value of the first frame image and the pixel value of the second frame image fall out of the second specific range.

3. The endoscope system according to claim 1,
wherein the reliability calculating unit calculates the reliability by further using a ratio between a pixel value of the first frame image and a pixel value of the second frame image corresponding to different wavelength ranges.

4. The endoscope system according to claim 3,
wherein the reliability calculating unit calculates the reliability by using a second signal ratio that is a ratio between a pixel value of the first frame image or a pixel value of the second frame image corresponding to a red wavelength range and a pixel value of the first frame image or a pixel value of the second frame image corresponding to a green wavelength range.

5. The endoscope system according to claim 1,
wherein the first frame image and the second frame image are successively captured.

6. An endoscope system comprising:
a processor configured to function as:
- an image acquiring unit that acquires a first frame image obtained by photographing a photographic subject and a second frame image obtained by photographing the photographic subject at a timing different from that of the first frame image;
- an oxygen saturation calculating unit that calculates an oxygen saturation by using the first frame image and the second frame image;
- a reliability calculating unit that calculates reliability of the oxygen saturation, calculated by the oxygen calculating unit, by using a signal ratio that is a ratio between a pixel value in a first specific wavelength range corresponding to a specific wavelength range of the first frame image and a pixel value in a second specific wavelength range corresponding to the specific wavelength range of the second frame image; and
- an information amount adjusting unit that adjusts an information amount of the oxygen saturation by using the reliability, wherein the reliability calculating unit calculates the reliability by using the signal ratio, a pixel value of the first frame image, and a pixel value of the second frame image, wherein the reliability calculating unit calculates first reliability by using the signal ratio, calculates second reliability by using the pixel value of the first frame image and the pixel value of the second frame image, and outputs, as the reliability, a minimum out of the first reliability and the second reliability, and wherein the second reliability
- is a constant value if the pixel value of the first frame image and the pixel value of the second frame image fall within a second specific range and
- is zero if one or more of the pixel value of the first frame image and the pixel value of the second frame image fall out of the second specific range.

7. An endoscope system comprising:
a processor configured to function as:
- an image acquiring unit that acquires a first frame image obtained by photographing a photographic subject and a second frame image obtained by photographing the photographic subject at a timing different from that of the first frame image;
- an oxygen saturation calculating unit that calculates an oxygen saturation by using the first frame image and the second frame image;
- a reliability calculating unit that calculates reliability of the oxygen saturation, calculated by the oxygen calculating unit, by using a signal ratio that is a ratio between a pixel value in a first specific wavelength range corresponding to a specific wavelength range of the first frame image and a pixel value in a second specific wavelength range corresponding to the specific wavelength range of the second frame image; and
- an information amount adjusting unit that adjusts an information amount of the oxygen saturation by using the reliability, wherein the reliability calculating unit calculates the reliability by using the signal ratio, a pixel value of the first frame image, and a pixel value of the second frame image, wherein the reliability calculating unit calculates the reliability by further using a ratio between a pixel value of the first frame image and a pixel value of the second frame image corresponding to different wavelength ranges, and wherein the reliability calculating unit calculates the reliability by using a third signal ratio that is a ratio between a pixel value of the first frame image or a pixel value of the second frame image corresponding to a blue wavelength range and a pixel value of the first frame image or a pixel value of the second frame image corresponding to a green wavelength range.

8. An endoscope system comprising:
a processor configured to function as:
- an image acquiring unit that acquires a first frame image obtained by photographing a photographic subject and a second frame image obtained by photographing the photographic subject at a timing different from that of the first frame image;
- an oxygen saturation calculating unit that calculates an oxygen saturation by using the first frame image and the second frame image;
- a reliability calculating unit that calculates reliability of the oxygen saturation, calculated by the oxygen calculating unit, by using a signal ratio that is a ratio between a pixel value in a first specific wavelength range corresponding to a specific wavelength range of the first frame image and a pixel value in a second specific wavelength range corresponding to the specific wavelength range of the second frame image; and an information amount adjusting unit that adjusts an information amount of the oxygen saturation by using the reliability, wherein the reliability calculating unit calculates the reliability by using the signal ratio, a pixel value of the first frame image, and a pixel value of the second frame image, wherein the reliability calculating unit calculates the reliability by further using a ratio between a pixel value of the first frame image and a pixel value of the second frame image corresponding to different wavelength ranges, wherein the reliability calculating unit calculates the reliability by using a second signal ratio that is a ratio between a pixel value of the first frame image or a pixel value of the second frame image corresponding to a red wavelength range and a pixel value of the first frame image or a pixel value of the second frame image corresponding to a green wavelength range, and wherein the reliability calculating unit calculates the reliability by using a third signal ratio that is a ratio between a pixel value of the first frame image or a pixel value of the second frame image corresponding to a blue wavelength range and a pixel value of the first frame image or a pixel value of the second frame image corresponding to a green wavelength range.

* * * * *